(12) United States Patent
Lu et al.

(10) Patent No.: US 7,745,590 B1
(45) Date of Patent: *Jun. 29, 2010

(54) DEGRADABLE MACROMOLECULAR MAGNETIC RESONANCE IMAGING CONTRAST AGENTS AND METHODS THEREOF

(75) Inventors: Zheng-Rong Lu, Salt Lake City, UT (US); Jindrich Kopecek, Salt Lake City, UT (US); Dennis L. Parker, Centerville, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1353 days.

This patent is subject to a terminal disclaimer.

(21) Appl. No.: 11/203,799

(22) Filed: Aug. 15, 2005

Related U.S. Application Data (63) Continuation-in-part of application No. 10/288,618, filed on Nov. 5, 2002, now Pat. No. 6,982,324.

(60) Provisional application No. 60/338,831, filed on Nov. 13, 2001.

(51) Int. Cl.
*C07F 5/00* (2006.01)

(52) U.S. Cl. ................ 534/15; 424/1.11; 424/1.65; 424/9.3; 424/9.34; 424/9.35; 424/9.36; 424/9.362; 424/9.363

(58) Field of Classification Search ........... 424/1.11, 424/1.21, 1.49, 1.53, 1.57, 1.69, 1.73, 9.1, 424/9.3, 9.4, 9.5, 9.6, 9.7, 9.8, 1.65, 9.34, 424/9.341, 9.35, 9.36, 9.361, 9.362, 9.363, 424/9.364, 9.32; 534/7, 10–16
See application file for complete search history.

(56) References Cited

U.S. PATENT DOCUMENTS 6,982,324 B1 * 1/2006 Lu et al. ................ 534/15

OTHER PUBLICATIONS

Silvia Arpicco et al., *Bioconjugate Chem.*, vol. 8, No. 3, pp. 327-337 (1997), "New Coupling Reagents for the Preparation of Disulfide Cross-Linked Conjugates with Increased Stability."

Zheng-Rong Lu et al., *Magnetic Resonance in Medicine*, vol. 51, pp. 27-34 (2004), "Extracellular Biodegradable Macromolecular Gadolinium (III) Complexes for MRI."

Aaron M. Mohs et al., *Bioconjugate Chem.*, vol. 15, No. 6, pp. 1424-1430 (2004), "PEG-g-poly(GdDTPA-co-L-cystine): A Biodegradable Macromolecular Blood Pool Contrast Agent for MR Imaging."

Yuda Zong et al., *Magnetic Resonance in Medicine*, vol. 53, pp. 835-842 (2005), "Contrast-Enhanced MRI With New Biodegradable Macromolecular Gd(III) Complexes in Tumor-Bearing Mice."

* cited by examiner

*Primary Examiner*—D L Jones
(74) *Attorney, Agent, or Firm*—Gardner Groff Greenwald & Villanueva, PC (57) ABSTRACT

Degradable macromolecular magnetic resonance imaging contrast agents for use in various diagnostic procedures, and methods for synthesizing, using and degrading these agents, are described. The macromolecule contrast agents disclosed in various aspects of this invention are degradable gadolinium compounds which show prolonged plasma retention, and enhanced permeability and retention in solid tumors, but are still capable of being rapidly cleared from the body.

20 Claims, 1 Drawing Sheet

*FIG. 1*

DEGRADABLE MACROMOLECULAR MAGNETIC RESONANCE IMAGING CONTRAST AGENTS AND METHODS THEREOF

CROSS-REFERENCE TO RELATED APPLICATIONS

This application is a continuation-in-part of application Ser. No. 10/288,618, filed Nov. 5, 2002 now U.S. Pat. No. 6,982,324, which claims the benefit of Provisional Application No. 60/338,831, filed Nov. 13, 2001, the disclosures of which are incorporated by reference.

BACKGROUND OF THE INVENTION

1. Field of the Invention

This invention relates generally to macromolecular contrast agents used in diagnostic imaging, and methods of synthesizing, using and degrading such compounds.

2. Description of the Related Art

Magnetic resonance imaging (MRI) is a non-invasive method for medical diagnosis. Paramagnetic metal complexes are often used as contrast agents to enhance the image contrast between normal tissue and diseased tissue. Paramagnetic metal ions that are typically used in diagnostic procedures include manganese ($Mn^{2+}$), iron ($Fe^{+3}$), and gadolinium ($Gd^{+3}$). Chelates of $Gd^{+3}$ are frequently used as MRI contrast agents because of their long electronic relaxation time and high magnetic moment. Gadolinium-based contrast agents include small molecular gadolinium complexes such as Gd(III)(DTPA) [diethylenetriaminepentaacetate] and Gd(III)(DOTA) [1,4,7,10-tetraazadodecanetetraacetic acid], and their derivatives. Use of stable, non-toxic paramagnetic chelates in conjunction with various diagnostic procedures, such as MRI, have been used in the prior art to increase the accuracy of diagnosis.

Macromolecular MRI contrast agents, sometimes referred to as long-circulating or blood pool agents, are particularly useful because of their prolonged retention time in the blood pool. These agents typically increase the magnetic resonance signal of blood by shortening the $T_1$ relaxation time of blood and can be used for a variety of diagnostic procedures, including magnetic resonance angiography. Because of the enhanced permeability and retention, these contrast agents accumulate effectively in solid tumors and have a potential in contrast enhancement in MR cancer imaging. However, the macromolecular contrast agents currently available to the medical community have poor clearance rates. As a result of poor clearance rates, use of Gd macromolecular agents may result in Gd accumulation in bone and other tissues, resulting in toxicity and adverse side-effects.

SUMMARY OF THE INVENTION

It is an object of several embodiments of the present invention to provide novel degradable macromolecular contrast agents which have the characteristics of prolonged blood circulation time and enhanced permeability and retention in solid tumors, but are still capable of being rapidly cleared from the body after diagnostic exams. In a preferred embodiment, these contrast agents are gadolinium complexes that are used in magnetic resonance imaging. In an alternative embodiment, the macromolecular Gd complexes are used in X-ray computed tomography. In other embodiments, the degradable polymer ligands can form chelates with radioactive metal ions for scintigraphy, positron emission tomography and radiotherapy.

In another aspect of the invention, the complexes include targeting molecules. The incorporation of targeting molecules, including, but not limited to, antibodies, antibody fragments, peptides, and other proteins results in macromolecular contrast agents with targeting ability.

It is another object of various aspects of the invention to provide a method for obtaining a magnetic resonance image of a tissue or organ of a mammal by administering one or more macromolecule contrast agents and obtaining a magnetic resonance image. In several embodiments, the macromolecule contrast agents are capable of being degraded by both endogenous and exogenous compounds. In one embodiment, the contrast agents are degraded by endogenous mercaptans.

It is a further object of various embodiments to degrade or stimulate degradation of the macromolecule contrast agents by administering one or more disulfide bond reducing compounds or other compounds that stimulate the degradation of the macromolecule contrast agents. In one embodiment, exogenous mercaptans are delivered to the mammal. Another object of several embodiments of the current invention is to administer macromolecule contrast agents in conjunction with other agents. In various aspects, physiologically acceptable agents, such as diluents and carriers, are also administered.

In a preferred embodiment, the current invention is a macromolecule contrast formulation comprising any one or more of the following macromolecule contrast agents, or physiologically acceptable salts thereof:

(Structure I)

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X and Y are independently selected from the group consisting of O and NH; and wherein n is an integer between 2 and 10,000;

(Structure II)

$$P\left\{X^{-R}\diagdown_{S}\diagdown^{S}\diagdown_{R'}\diagup^{Y}\diagdown[Gd(III)L]\right\}_n$$

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;
wherein X and Y are independently selected from the group consisting of amide groups, ester groups, urea groups, thiourea groups, carbonate groups, carbamate groups, ether bonds and thioether bonds;
wherein P is selected from the group consisting of water soluble polymer chains, dendrimers, polysaccharides, peptides, proteins, polymer-peptide conjugates and polymer-protein conjugates;
wherein n is an integer between 2 and 10,000; and
wherein L is selected from the group consisting of diethylenetriaminepentaacetate (DTPA) or its derivatives, 1,4,7,10-tetraazadodecanetetraacetate (DOTA) and its derivatives, 1,4,7,10-tetraazadodecane-1,4,7-triacetate (DO3A) and its derivatives, ethylenediaminetetraacetate (EDTA) and its derivatives, 1,4,7,10-tetraazacyclotridecanetetraacetic acid (TRITA) and its derivatives, 1,4,8,11-tetraazacyclotetradecane-1,4,8,11-tetraacetic acid (TETA) and its derivatives, 1,4,7,10-tetraazadodecanetetramethylacetate (DOTMA) and its derivatives, 1,4,7,10-tetraazadodecane-1,4,7-trimethylacetate (DO3MA) and its derivatives, N,N',N'',N'''-tetraphosphonatomethyl-1,4,7,10-tetraazacyclododecane (DOTP) and its derivatives, 1,4,7,10-tetraazacyclododecane-1,4,7,10-tetrakis(methylene methylphosphonic acid) (DOTMP) and its derivatives, 1,4,7,10-tetraazacyclododecane-1,4,7,10-tetrakis(methylene phenylphosphonic acid) (DOTPP) and its derivatives and other chelating ligands;

(Structure III)

$$\left[P\diagdown_{X}\diagdown^{R}\diagdown_{S}\diagdown^{S}\diagdown_{R'}\diagdown^{Y}\diagdown\text{...DTPA-Gd}^{3+}\text{...}\right]_n$$

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;
wherein X is selected from the group consisting of amide groups, ester groups, and ether bonds;
wherein Y is selected from the group consisting of O and NH;
wherein n is an integer between 2 and 10,000; and
wherein P is selected from the group consisting of water soluble polymer chains, dendrimers, polysaccharides, peptides, proteins, polymer-peptide conjugates and polymer-protein conjugates;

(Structure IV)

$$\left[P\diagdown_{X}\diagdown^{R}\diagdown_{S}\diagdown^{S}\diagdown_{R'}\diagdown^{Y}\diagdown\text{...DOTA-Gd}^{3+}\text{...}\right]_n$$

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;
wherein X is selected from the group consisting of amide groups, ester groups, and ether bonds;
wherein Y is selected from the group consisting of O and NH;
wherein n is an integer between 2 and 10,000; and
wherein P is selected from the group consisting of water soluble polymer chains, dendrimers, saccharides, peptides, proteins, polymer-peptide conjugates and polymer-protein conjugates;

(Structure V)

$$\left[P\diagdown_{X}\diagdown^{R}\diagdown_{S}\diagdown^{S}\diagdown_{R'}\diagdown\text{N(H)C(S)N(H)-Ph-DOTA-Gd}^{3+}\right]_n$$

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;
wherein X is selected from the group consisting of amide groups, ester groups, and ether bonds;
wherein Y is selected from the group consisting of O and NH;
wherein n is an integer between 2 and 10,000; and
wherein P is selected from the group consisting of water soluble polymer chains, dendrimers, polysaccharides, peptides, proteins, polymer-peptide conjugates and polymer-protein conjugates;

(Structure VI)

wherein R, R', R" and R'" are independently selected from the group consisting of H, $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X is selected from the group consisting of O and NH; and wherein n is an integer between 2 and 10,000;

(Structure VII)

wherein R and R' are independently selected from the group consisting of H, $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X is selected from the group consisting of O and NH; and wherein n is an integer between 2 and 10,000.

One embodiment comprises one or more of the following molecular contrast agents:

(Agent 1)

-continued (Agent 7)

(Agent 8)

(Agent 9)

(Agent 10)

-continued (Agent 11)

wherein n is an integer between 2 and 10,000; and wherein x is an integer between 1 and 20; and wherein m is an integer between 0 and 10,000.

One aspect of the invention includes a method for obtaining a magnetic resonance image of a tissue or organ of a mammal by administering an effective amount of one or more macromolecule contrast agents to the mammal and obtaining a magnetic resonance image. In a preferred embodiment, one or more of the macromolecule contrast agents are degraded by endogenous mercaptans.

According to one aspect of the invention, one or more compounds that stimulate the degradation of said macromolecule contrast agent is also administered. In another aspect, one or more disulfide bond reducing compounds is also administered. The disulfide bond reducing compound is selected from the group consisting of one or more of the following: mercaptans, NADH, NADPH, hydrazines, phosphines, zinc, tin(II), sodium sulfide, performic acid, hydrogen peroxide.

Mercaptans used in various aspects of the present invention are selected from the group consisting of one or more of the following: cysteine and its derivatives, glutathione and its derivatives, cysteinylglycine and its derivatives, 2,3-dimercaptosuccinic acid and its derivatives, 2,3-dimercapto-1-propanesulfonic acid and its derivatives, 2-mercaptoethanol, penicillamine and its derivatives, mercaptoacetic acid and its derivatives, mercaptoanisole, 2-mercaptobenzoic acid and its derivatives, 4-mercaptobenzoic acid and its derivatives, 2-mercapto-5-benzimidazolesulfonic acid and its derivatives, 2-mercaptobenzothiazole, 3-mercapto-iso-butyric acid, mercaptocyclohexane, 2-mercaptoethanesulfonic acid, 2-mercaptoethylamine, 2-mercaptoethylamine hydrochloride, 3-mercapto-1,2-propanediol, 3-mercapto-1-propanesulfonic acid, 3-mercapto-1-propanol, 2-mercaptopropionic acid, 3-mercaptopropionic acid, diethyldithiocarbamate, dithioerythritol, and dithioglycol.

According to one aspect of the invention, two or more of macromolecule contrast agents are administered simultaneously. In one embodiment, the macromolecule contrast formulation comprises a first macromolecule contrast agent and a second macromolecule contrast agent, wherein the second macromolecule contrast agent is administered after the administration of said first macromolecule contrast agent.

In another embodiment, at least one of the macromolecule contrast agents is administered in conjunction with one or more physiologically acceptable agents selected from the group consisting of: diluents, carriers, antibodies, antibody Fab' fragments, antibody F(ab')$_2$ fragments, and delivery systems.

In a preferred embodiment, at least one of the macromolecule contrast agents is administered in conjunction with one or more contrast agents selected from the group consisting of: paramagnetic metal complexes, radioactive metal complexes, therapeutic agents, proteins, DNA, RNA, drug delivery systems and gene delivery systems.

It is an object of several embodiments of the current invention to obtain a magnetic resonance image of healthy or tumorous tissues or organs, including but not limited to, liver, spleen, lung, heart, kidney, tumors, ovary, pancreas, biliary system, peritoneum, muscles, head, neck, esophagus, bone marrow, lymph node, lymph vessels, nervous system, brain, spinal cord, blood capillaries, stomach, small intestine, and large intestine.

DETAILED DESCRIPTION OF THE PREFERRED EMBODIMENT

In a preferred embodiment of the present invention, degradable macromolecular MRI contrast agents having degradable disulfide bond in the polymer backbone are disclosed. An alternative embodiment includes degradable macromolecular MRI contrast agents which contain a structure that conjugates the paramagnetic metal complexes, Gd(DTPA), Gd(DOTA) or their derivatives, to polymer or protein carriers through a disulfide bond. In several embodiments, the disulfide bond can readily be reduced by one or more mercaptans or thiols, including, but not limited to cysteine, N-acetylcysteine, glutathione, and the like. These mercaptans may be endogenously available or exogenously delivered. Alternatively, compounds that stimulate the endogenous degradation of macromolecule contrast agents may also be delivered using several embodiments of the current invention, including, but not limited to, cysteine, N-acetylcysteine, glutathione, cysteinylglycine, and homocysteine. One skilled in the art will appreciate that several agents capable of reducing disulfide bonds may be used according to various aspects of this invention, including, but not limited to cysteine, N-acetylcysteine, glutathione, cysteinylglycine, and their derivatives.

Another object of several embodiments is to provide a method for obtaining a magnetic resonance image of a tissue or organ of a mammal by administering an effective amount of one or more macromolecule contrast agents to the mammal and obtaining a magnetic resonance image. One skilled in the art will understand that many known methods of obtaining magnetic resonance image exist in the scientific and medical field. In a preferred embodiment, an MRI procedure is performed on a human subject. One skilled in the art will appreciate that a variety of tissues and organs may be examined using different aspects of this invention, including, but not limited to, liver, spleen, lung, esophagus, bone marrow, lymph node, lymph vessels, nervous system, brain, spinal cord, blood capillaries, stomach, small intestine, large intestine. One skilled in the art will appreciate that both normal tissues and abnormal tissues, such as tumors, can be examined.

Another aspect of this invention relates to a method of clearing metal complexes. Preferably, the clearance procedure is performed after the MRI procedure has been completed or substantially completed. In one embodiment, mercaptans, or other similar agents, are administered after the MRI procedure. In various embodiments, these agents facilitate the clearing process by cleaving the macromolecular backbone. Alternatively, or in addition, clearing occurs by removal of the paramagnetic metal complexes from the polymer carriers by cleavage of the disulfide bond. Several embodiments are particularly advantageous because the paramagnetic metal complexes released from the macromolecules can be cleared at a rate comparable to that of the small molecular contrast agents used clinically today.

In a preferred embodiment, the macromolecular compounds have a prolonged retention time in the blood pool, favorable accumulation in the solid tumor tissues, and are cleared rapidly after MRI. These macromolecular agents, and the methods described thereof, will be indispensable tools in a variety of medical procedures, including, but not limited to, angiography, plethysmography, lymphography, mammography, cancer diagnosis, and functional and dynamic MRI.

Chemical Compounds

The macromolecular MRI contrast agents disclosed in accordance with various embodiments of the present invention are represented by the following generic formulae:

(Structure I)

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X and Y are independently selected from the group consisting of O and NH; and wherein n is an integer between 2 and 10,000.

(Structure II)

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X and Y are independently selected from the group consisting of amide groups, ester groups, urea groups, thiourea groups, carbonate groups, carbamate groups, ether bonds and thioether bonds;

wherein P is selected from the group consisting of water soluble polymer chains, dendrimers, polysaccharides, peptides, proteins, polymer-peptide conjugates and polymer-protein conjugates;

wherein n is an integer between 2 and 10,000; and wherein L is selected from the group consisting of diethylenetriaminepentaacetate (DTPA) or its derivatives, 1,4,7,10-tetraazadodecanetetra-acetate (DOTA) and its derivatives, 1,4,7,10-tetraazadodecane-1,4,7-triacetate (DO3A) and its derivatives, and any other chelating ligands.

(Structure III)

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X is selected from the group consisting of amide groups, ester groups, urea groups, thiourea groups, carbonate groups, carbamate groups, ether bonds and thioether bonds;

wherein Y is selected from the group consisting of O and NH;

wherein n is an integer between 2 and 10,000; and wherein P is selected from the group consisting of water soluble polymer chains, dendrimers, polysaccharides, peptides, proteins, polymer-peptide conjugates and polymer-protein conjugates.

(Structure IV)

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X is selected from the group consisting of amide groups, ester groups, urea groups, thiourea groups, carbonate groups, carbamate groups, ether bonds and thioether bonds;

wherein Y is selected from the group consisting of O and NH;

wherein n is an integer between 2 and 10,000; and wherein P is selected from the group consisting of water soluble polymer chains, dendrimers, polysaccharides, peptides, proteins, polymer-peptide conjugates and polymer-protein conjugates.

(Structure V)

wherein R and R' are independently selected from the group consisting of $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X is selected from the group consisting of amide groups, ester groups, urea groups, thiourea groups, carbonate groups, carbamate groups, ether bonds and thioether bonds;

wherein n is an integer between 2 and 10,000; and wherein P is selected from the group consisting of water soluble polymer chains, dendrimers, polysaccharides, peptides, proteins, polymer-peptide conjugates and polymer-protein conjugates.

(Structure VI)

wherein R, R', R" and R'" are independently selected from the group consisting of H, $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X is selected from the group consisting of O and NH; and wherein n is an integer between 2 and 10,000.

(Structure VII)

wherein R and R' are independently selected from the group consisting of H, $C_1$ to $C_{18}$ alkyls, substituted alkyls, aryls, one or more functional groups containing alkyl, aryl or polyethylene glycol, saccharides, amino acids, peptides, proteins, peptide conjugates and protein conjugates;

wherein X is selected from the group consisting of O and NH; and wherein n is an integer between 2 and 10,000.

The macromolecular MRI contrast agents disclosed in accordance with various embodiments of the present invention are represented by the following formulae:

(Poly(L-glutamic acid)-cystamine-[Gd(DTPA)] conjugate)

wherein n is an integer between 2 and 10,000; and wherein m is an integer between 0 and 10,000.

(Poly(L-glutamic acid)-cystamine-[Gd(DOTA)] conjugate)

wherein n is an integer between 2 and 10,000; and wherein m is an integer between 0 and 10,000.

(HPMA copolymer-cystamine-[Gd(DPTA)]
conjugate)

wherein n is an integer between 2 and 10,000; and
wherein m is an integer between 0 and 10,000.

(Agent 4)

(HPMA copolymer-cystamine-[Gd(DOTA)]
conjugate)

wherein n is an integer between 2 and 10,000; and
wherein m is an integer between 0 and 10,000.

(Agent 5)

(HPMA copolymer-cystamine-[Gd(DOTA)]
conjugate)

wherein n is an integer between 2 and 10,000; and
wherein m is an integer between 0 and 10,000.

(Agent 6)

(Poly(L-glutamic acid)-cystamine-[Gd(DOTA)] conjugate)

wherein n is an integer between 2 and 10,000; and
wherein m is an integer between 0 and 10,000.

(Agent 7)

(Poly(L-glutamic acid)-cystamine-[Gd(DTPA)] conjugate)

wherein n is an integer between 2 and 10,000; and
wherein m is an integer between 0 and 10,000.

(Agent 8)

(DTPA cystamine copolymer Gd (III) complex)

wherein n is an integer between 2 and 10,000.

(Agent 9)

(DTPA-cystamine-polyethylene glycols copolymer Gd³⁺ complex)

wherein n is an integer between 2 and 10,000.

(Agent 10)

(Poly(L-glutamic acid)-cystine amide-[Gd(DOTA)] conjugate)

wherein n is an integer between 2 and 10,000; and
wherein m is an integer between 0 and 10,000.

(Agent 11)

(Antibody Fab' fragment-poly(L-glutamic acid)-cystine amide-[Gd(DOTA)] conjugate)

wherein n is an integer between 2 and 10,000; and
wherein x is an integer between 1 and 20; and
wherein m is an integer between 0 and 10,000.

As discussed above, some embodiments of the disclosed compounds comprise one or more polyethylene glycol (PEG) groups, for example, the P, R, and/or R' groups in Structures I-VII. In some embodiments, the PEG groups independently have molecular weights of at least about 50 Daltons, at least about 500 Daltons, at least about 1000 Daltons, or at least about 2000 Daltons. In some embodiments, the molecular weights of PEG groups are independently from about 50 Daltons to about 50,000 Daltons.

Synthesis Reactions

Synthesis of (DTPA-Gd)-cystamine copolymer

Cystamine dichloride (0.63 g, 2.8 mmol) and triethylamine (2 ml, excess) were mixed with 20 ml DMSO (anhydrous), followed by DTPA dianhydride (1 g, 2.8 mmol). The mixture was stirred at room temperature for 2 days. The product was precipitated in acetone. The precipitate was collected by filtration and washed with acetone. The product was then dissolved in deionized water and dialyzed (MWCO 6,000-8,000

Figure 1:
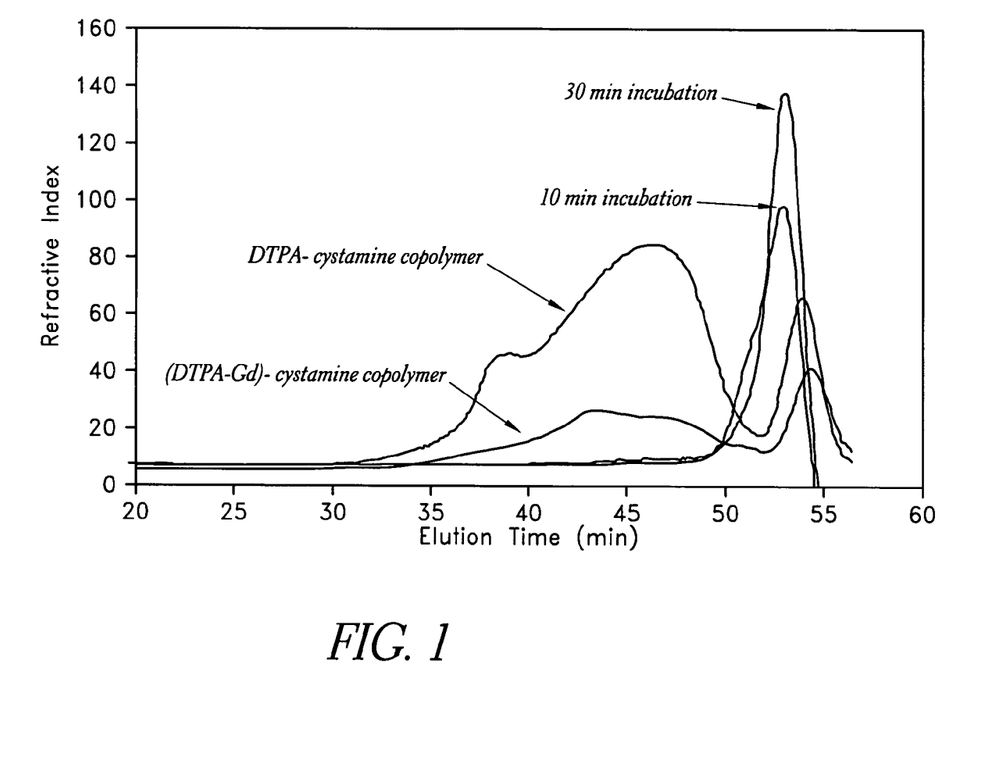
FIG. 1 shows size exclusion chromatograms of DPTA-cystamine copolymer, (DPTA-Gd)-cystamine copolymer and the degradation mixtures of (DPTA-Gd)-cysteine copolymer with cysteine at 37° C. for 10 minutes and 30 minutes, respectively.

Da) for 2 days. The solution was then lyophilized, giving 550 mg (34%) DTPA-cystamine copolymer, indicated as (A) below. The copolymer was characterized by size exclusion chromatography (FIG. 1). DTPA-cystamine copolymer (300 mg) was dissolved in 2 ml DI water and $GdCl_3$ was added with xylene orange as an indicator. The solution was neutralized with NaOH to pH 5.0. The resulting solution was passed through a Sephadex G-25 column to remove excess $GdCl_3$ and salt. Finally, the product was lyophilized giving a colorless product, (DTPA-Gd) cystamine copolymer, indicated as (B) below. The yield was 250 mg, or 83%. The product was characterized by size exclusion chromatography (SEC), FIG. 1.

Synthesis of HPMA copolymer-(DTPA-Gd) conjugate

Cystamine hydrochloride (400 mg excess) and triethylamine (1.0 ml, excess) were dissolved in 20 ml methanol, and HPMA copolymer with p-nitrophenyl active ester (Mn=18,300 Da and Mw=22,500 Da, ONp %=9.6 mol-%) (420 mg) in 5 ml methanol was added dropwise to above solution with stirring. The mixture was stirred overnight at room temperature. The solution was concentrated under vacuum and applied to Sephadex LH-20 column to separate the polymer conjugate, eluted with methanol. The polymer fraction was collected and solvent was removed under vacuum giving HPMA copolymer-cystamine conjugates. The product was dissolved in water, and DTPA dianhydride (300 mg, excess) was added to the solution. The mixture was stirred for 30 minutes, and pH was adjusted to 7.0 with $NaHCO_3$. The mixture was stirred at room temperature overnight. The polymer was separated from excess DTPA by passing through a Sephadex G-25 column, eluted with water. $GdCl_3$ was added with xylene orange as an indicator. The solution was neutralized with NaOH to pH 5.0. The resulting solution was passed through a Sephadex G-25 column to remove excess $GdCl_3$ and salt. Finally, the product was lyophilized giving a colorless product, HPMA copolymer-[DTPA-Gd] conjugate, indicated as (C) below. The yield was 340 mg, or 85%.

Degradation of (DTPA-Gd)-cystamine copolymer

The (DTPA-Gd)-cystamine copolymer (5 mg) was dissolved in PBS buffer (1.0 ml, pH 7.4) and incubated with cysteine (1 mM) at 37° C. for 10 mM and 30 mM, respectively. The degradation reaction, (D), is shown below. The reaction mixture was analyzed by size exclusion chromatography with an analytical Superose 6 column, FIG. 1. Results indicated that the macromolecular MRI contrast agent, (DTPA-Gd)-cystamine copolymer, was completely degraded into small molecules by cysteine during a very short incubation period.

(A)
(DTPA cystamine copolymer)

(B)
([DTPA-Gd]) cystamine copolymer)

(C)
(HPMA copolymer-[Gd(DPTA)] conjugates)

(D)

(Degradation of the (DPTA-Gd)-cystamine copolymers by cysteine)

Administration

Suitable dosages of the macromolecule contrast agents disclosed in several embodiments of the current invention will generally range from about 0.001 mmol to about 10 mmol gadolinium per kg body weight, more preferably, between about 0.01 mmol and 1.0 mmol gadolinium per kg body weight. The compounds are preferably administered systemically, as appropriately determined by one skilled in the art. More preferably, the contrast agents are administered intravenously. However, these agents may be delivered subcutaneously, or by any other route which may be effective in providing systemic dosing of the agent. In one embodiment of the current invention, two or more of the macromolecule contrast agents are administered simultaneously. In an alternative embodiment, a second macromolecule contrast agent is administered after the delivery of a first macromolecule contrast agent. In one embodiment of the present invention, one or more macromolecule contrast agents may be administered in conjunction with one or more physiologically acceptable diluents, carriers or other contrast agents.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A macromolecule contrast agent comprising a compound according to the following formula:

wherein R and R' are independently selected from the group consisting of $C_1$ to $C_{18}$ alkyls, substituted alkyls, aryls, polyethylene glycol, saccharides, amino acids, peptides, proteins, peptide conjugates and protein conjugates, and combinations of at least two of alkyl, aryl, and polyethylene glycol groups;

wherein X and Y are independently selected from the group consisting of amide groups, ester groups, urea groups, thiourea groups, carbonate groups, carbamate groups, ether bonds and thioether bonds;

wherein P is selected from the group consisting of water soluble polymer chains, dendrimers, polysaccharides, peptides, proteins, polymer-peptide conjugates and polymer-protein conjugates;

wherein n is an integer between 2 and 10,000; and wherein L is selected from the group consisting of diethylenetriaminepentaacetate (DTPA), 1,4,7,10-tetraazadodecanetetraacetate (DOTA), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-trimethylacetate (DO3MA), N,N',N'',N'''-tetraphosphonatomethyl-1,4,7,10-tetraazacyclododecane (DOTP), 1,4,7,10-tetraazacyclododecane-1,4,7,10-tetrakis (methylene methylphosphonic acid) (DOTMP), and 1,4,7,10-tetraazacyclododecane-1,4,7,10-tetrakis(methylene phenylphosphonic acid) (DOTPP).

2. The macromolecule contrast agent of claim 1, wherein at least one of R and R' comprises polyethylene glycol with a molecular weight of from about 50 Daltons to about 50,000 Daltons.

3. A macromolecule contrast agent comprising a compound according to the following formula:

wherein R and R' are independently selected from the group consisting of $C_1$ to $C_{18}$ alkyls, substituted alkyls, aryls, polyethylene glycol, saccharides, amino acids, peptides, proteins, peptide conjugates and protein conjugates, and combinations of at least two of alkyl, aryl, and polyethylene glycol groups;

wherein X is selected from the group consisting of amide groups, ester groups, and ether bonds;

wherein Y is selected from the group consisting of O and NH;

wherein n is an integer between 2 and 10,000; and wherein P is selected from the group consisting of water soluble polymer chains, dendrimers, polysaccharides, peptides, proteins, polymer-peptide conjugates and polymer-protein conjugates.

4. The macromolecule contrast agent of claim 3, wherein at least one of R and R' comprises polyethylene glycol with a molecular weight of from about 50 Daltons to about 50,000 Daltons.

5. A macromolecule contrast agent comprising a compound according to the following formula:

wherein R and R' are independently selected from the group consisting of $C_1$ to $C_{18}$ alkyls, substituted alkyls, aryls, polyethylene glycol, saccharides, amino acids, peptides, proteins, peptide conjugates and protein conjugates, and combinations of at least two of alkyl, aryl, and polyethylene glycol groups;

wherein X is selected from the group consisting of amide groups, ester groups, and ether bonds;

wherein Y is selected from the group consisting of O and NH;

wherein n is an integer between 2 and 10,000; and wherein P is selected from the group consisting of water soluble polymer chains, dendrimers, polysaccharides, peptides, proteins, polymer-peptide conjugates and polymer-protein conjugates.

6. The macromolecule contrast agent of claim 5, wherein at least one of R and R' comprises polyethylene glycol with a molecular weight of from about 50 Daltons to about 50,000 Daltons.

7. A macromolecule contrast agent comprising a compound according to the following formula:

wherein R and R' are independently selected from the group consisting of $C_1$ to $C_{18}$ alkyls, substituted alkyls, aryls, polyethylene glycol, saccharides, amino acids, peptides, proteins, peptide conjugates and protein conjugates, and combinations of at least two of alkyl, aryl, and polyethylene glycol;

wherein X is selected from the group consisting of amide groups, ester groups, and ether bonds;

wherein Y is selected from the group consisting of O and NH;

wherein n is an integer between 2 and 10,000; and wherein P is selected from the group consisting of water soluble polymer chains, dendrimers, polysaccharides, peptides, proteins, polymer-peptide conjugates and polymer-protein conjugates.

8. The macromolecule contrast agent of claim 7, wherein at least one of R and R' comprises polyethylene glycol with a molecular weight of from about 50 Daltons to about 50,000 Daltons.

9. A macromolecule contrast agent comprising a compound selected from the group consisting of compounds according to the following formulae:

(Compound 2)

-continued (Compound 4)

(Compound 5)

(Compound 6)

(Compound 7)

wherein n is an integer between 2 and 10,000; and
wherein x is an integer between 1 and 20; and
wherein m is an integer between 0 and 10,000.

10. A method for obtaining a magnetic resonance image of a tissue or organ of a mammal comprising administering an effective amount of one or more macromolecule contrast agents of claim 1 to the mammal and obtaining a magnetic resonance image of the tissue or organ.

11. The method of claim 10, wherein the tissue or organ comprises the liver, spleen, lung, esophagus, bone marrow, lymph node, lymph vessels, nervous system, brain, spinal cord, blood capillaries, stomach, small intestine, or large intestine.

12. The method of claim 10, wherein the method is performed during a medical procedure selected from the group consisting of angiography, plethysmography, lymphography, mammography, cancer diagnosis, functional MRI and dynamic MRI.

13. The method of claim 10, wherein one or more disulfide bond reducing compounds are administered with the contrast agent.

14. The method of claim 10, wherein the disulfide bond reducing compound is selected from the group consisting of one or more mercaptans, NADH, NADPH, hydrazines, phosphines, zinc, tin(II), sodium sulfide, performic acid, and hydrogen peroxide.

15. The method of claim 14, wherein the mercaptan is selected from the group consisting of cysteine, glutathione, cysteinylglycine and its derivatives, 2,3-dimercaptosuccinic acid, 2,3-dimercapto-1-propanesulfonic acid and its derivatives, 2-mercaptoethanol, penicillamine and its derivatives, mercaptoacetic acid, mercaptoanisole, 2-mercaptobenzoic acid, 4-mercaptobenzoic acid, 2-mercapto-5-benzimidazole-sulfonic acid, 2-mercaptobenzothiazole, 3-mercapto-iso-butyric acid, mercaptocyclohexane, 2-mercaptoethanesulfonic acid, 2-mercaptoethylamine, 2-mercaptoethylamine hydrochloride, 3-mercapto-1,2-propanediol, 3-mercapto-1-propanesulfonic acid, 3-mercapto-1-propanol, 2-mercaptopropionic acid, 3-mercaptopropionic acid, diethyldithiocarbamate, dithioerythritol, and dithioglycol.

16. The method of claim 10, wherein the contrast agent comprises a targeting molecule.

17. The method of claim 16, wherein the targeting molecule comprises an antibody, an antibody fragment, a peptide, or a protein.

18. The method of claim 10, wherein two or more of macromolecule contrast agents are administered simultaneously.

19. The method of claim 10, wherein the macromolecule contrast agent comprises a first macromolecule contrast agent and a second macromolecule contrast agent, wherein the second macromolecule contrast agent is administered after the administration of said first macromolecule contrast agent.

20. The method of claim 10, wherein one or more contrast agents selected from the group consisting of paramagnetic metal complexes, radioactive metal complexes, proteins, DNA, and RNA, is administered in conjunction with the macromolecule contrast agent.

* * * * *